United States Patent [19]

Hilfman

[11] 4,194,058

[45] Mar. 18, 1980

[54] PROCESS FOR THE CONVERSION OF AROMATIC HYDROCARBONS

[75] Inventor: Lee Hilfman, Mt. Prospect, Ill.

[73] Assignee: UOP Inc., Des Plaines, Ill.

[21] Appl. No.: 973,305

[22] Filed: Dec. 26, 1978

Related U.S. Application Data

[63] Continuation-in-part of Ser. No. 810,323, Jun. 27, 1977, Pat. No. 4,148,759, which is a continuation-in-part of Ser. No. 684,055, May 6, 1976, abandoned.

[51] Int. Cl.² ........................... C07C 3/52; C07C 3/62
[52] U.S. Cl. .................................. 585/455; 585/467; 585/475
[58] Field of Search ........... 260/668 H, 671 R, 671 C, 260/672 T; 252/455 Z; 585/455, 467, 475

[56] References Cited

U.S. PATENT DOCUMENTS

| | | | |
|---|---|---|---|
| 3,464,929 | 9/1969 | Mitsche | 260/672 T |
| 3,720,726 | 3/1973 | Mitsche et al. | 260/672 T |

*Primary Examiner*—C. Davis
*Attorney, Agent, or Firm*—James R. Hoatson, Jr.; John G. Cutts, Jr.; William H. Page, II

[57] ABSTRACT

Process for the conversion of aromatic hydrocarbons. Especially useful for the reaction of an alkylating agent, preferably propylene, with an aromatic hydrocarbon. Novel feature is the use of a catalyst comprising nickel, molybdenum, platinum and a zeolitic carrier material.

9 Claims, 1 Drawing Figure

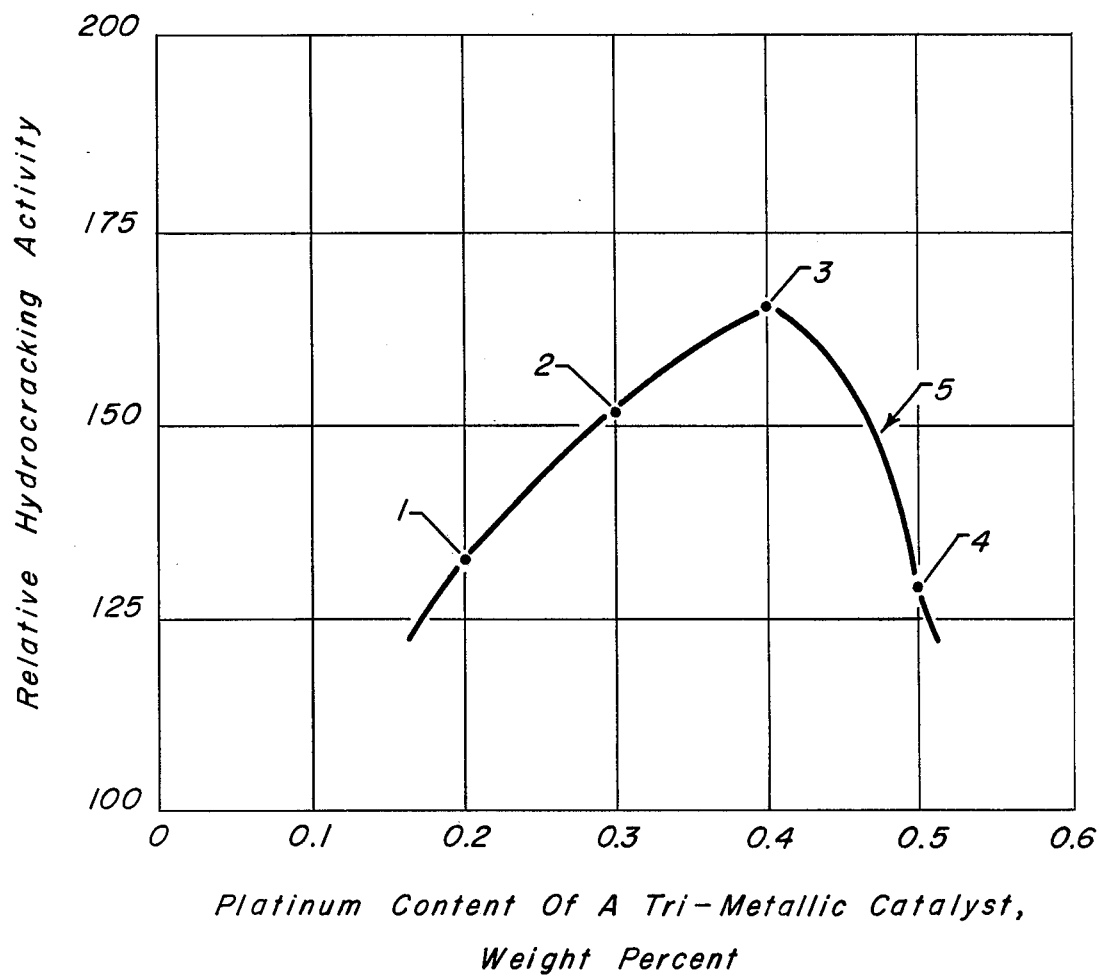

PROCESS FOR THE CONVERSION OF AROMATIC HYDROCARBONS

CROSS REFERENCE TO RELATED APPLICATION

This application is a continuation-in-part of my prior, copending application Ser. No. 810,323 filed on June 27, 1977, now U.S. Pat. No. 4,148,759, which is a continuation-in-part of my application Ser. No. 684,055 filed on May 6, 1976, now abandoned. The teachings of these prior applications are specifically incorporated herein by reference thereto.

BACKGROUND OF THE INVENTION

FIELD OF THE INVENTION

The present invention relates to an improved process for the conversion of an aromatic hydrocarbon in the presence of a nickel, molybdenum, platinum and a zeolitic carrier material catalyst system. The invention will be described with reference to alkylation, e.g., the synthesis of cumene by alkylation of benzene with propylene in the presence of the catalyst. The invention may also include alkylaromatic transalkylation.

DESCRIPTION OF THE PRIOR ART

Conversion of aromatic hydrocarbons is well known in industry. Some of the aromatic conversion reactions which occur include alkylation of aromatic hydrocarbons with an alkylating agent such as an olefin, disproportionation or transalkylation of alkylaromatic hydrocarbons and isomerization of alkylaromatic hydrocarbons such as xylenes, and of dialkyl and higher substituted aromatics.

Of special interest, has been the propylation of benzene to cumene. Cumene is used for the production of phenol and acetone. Cumene is also dehydrogenated to form methylstyrene, in a process similar to that used to convert ethylbenzene to styrene. Cumene is also used as a blending component in aviation gasoline because of its high octane number. The consumption of cumene in the U.S.A. was about 350,000 metric tons in 1968. Of this total, 94% was used for the production of phenol or acetone.

It is well known that cumene can be synthesized from benzene and propylene using a catalyst of $AlCl_3$, SPA or $BF_3$. SPA is a generally accepted abbreviation for solid phosphoric acid catalyst, or phosphoric acid which is absorbed on kieselguhr or other support.

$AlCl_3$ is a very popular alkylation catalyst, because of its high activity. Unfortunately, the catalyst operates as a slurry or sludge which is messy to handle on a commercial scale, and also is corrosive. The highly reactive nature of this Friedel-Crafts metal halide catalyst, $AlCl_3$, is desirable when attempting to alkylate benzene with ethylene, because less active catalyst systems do not work. However, for alkylation with propylene such highly reactive systems are not necessary.

Another highly selective catalyst system has been developed for the alkylation of benzene with olefins. This catalyst comprises boron trifluoride. The boron trifluoride catalyst system is exceptionally active and permits operation with dilute olefin streams, but it requires the continuous addition of $BF_3$ to maintain catalyst activity. High catalyst activity also leads to oligomerization of olefins so contact time of olefins with $BF_3$ catalyst should be as short as possible. This catalyst is also exceptionally water sensitive, as water not only destroys the catalyst, but produces very corrosive solutions which attack downstream processing units. $BF_3$ also frequently appears in the product and must be removed therefrom.

Because of the interest in alkylating benzene with propylene to make cumene, and because of the inadequacies of existing catalyst systems, I studied the work that others had done, and made exhaustive investigations to determine if it would be possible to find a catalyst which would have the activity and selectivity required to produce an acceptable cumene product, while making maximum use of existing petroleum resources and provide an improved process for the manufacture of cumene.

A highly active catalyst was sought to operate with less catalyst and to reduce operating or construction cost. In new units this would mean smaller, and cheaper reactor vessels, while in existing units it would mean that an increase in capacity could be obtained merely by changing catalyst in an existing reactor vessel with only minor modifications of the plant.

High selectivity is necessary, not only to permit operation with feedstreams which are not 100% pure propylene, but also to maximize production of the desired cumene product, and to minimize production of polymerized olefins, or polyalkylated aromatic compounds.

Accordingly, many catalyst systems were studied to find a catalyst with excellent activity and selectivity, which was not corrosive or destroyed by water.

The present invention provides a process for the catalytic conversion of an aromatic hydrocarbon comprising contacting the aromatic hydrocarbon with a reactant in the presence of a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum, and recovering a converted aromatic hydrocarbon as a product of the process.

DETAILED DESCRIPTION

The catalyst of the present invention comprises a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum. This novel catalytic composite has exceptional activity, selectivity and resistance to deactivation when employed in a hydrocarbon conversion process.

I have discovered an improved catalyst comprising nickel-molybdenum-platinum on a zeolitic support or carrier material. More specifically, I have discovered that an unusually superior catalyst results if the platinum content is from about 0.2 to about 0.5 weight percent on an elemental basis. The criticality of the range of the platinum concentration is further illustrated hereinbelow.

A particularly preferred catalyst support or base comprises a zeolite and alumina. In addition to the foregoing compositional limitations, it is important that the catalyst base have adequate pore volume, that is, a pore volume of at least 0.5 cc/g and preferably at least 0.6 cc/g or even 0.7 cc/g.

The zeolite-alumina catalyst base is preferably in the zerogel state, that is, it is dried sufficiently to afford the usual microporous structure and therefore an appreciable available surface.

In one embodiment accordingly, the present invention provides a method of preparing catalytic composites having hydrocracking activity comprising the steps: (a) preparing a zeolite-alumina carrier material; (b) impregnating said zeolite-alumina carrier material with a nickel component, a molybdenum component and a platinum component in amounts sufficient to result in the composite containing, on an elemental basis, about 1 to about 15 weight percent nickel, about 1 to about 10 weight percent molybdenum and about 0.2 to about 0.5 weight percent platinum.

In a second embodiment, the present invention relates to a process for the conversion of aromatic hydrocarbons which process comprises reacting said hydrocarbons in a reaction zone containing a catalytic composite prepared by a method comprising the steps: (a) preparing a zeolite-containing carrier material; (b) impregnating said carrier material with a nickel component, a molybdenum component and a platinum component in amounts sufficient to result in the composite containing, on an elemental basis, about 1 to about 15 weight percent nickel, about 1 to about 10 weight percent molybdenum and about 0.2 to about 0.5 weight percent platinum.

When it is desired to use the catalyst system in an alkylaromatic isomerization process, then alkylaromatic isomerization reaction conditions should be used. Reaction conditions are disclosed in U.S. Pat. No. 3,637,881 (Class 260-668a), the teachings of which are incorporated by reference. When it is desired to use the catalyst system of the present invention for alkylaromatic transalkylation then appropriate reaction conditions should also be used. These are disclosed in U.S. Pat. No. 3,720,726 (Class 260-672t), the teachings of which are incorporated by reference. Reaction conditions for the alkylation of aromatic hydrocarbons will be discussed in detail in a latter part of this specification.

Other objects and embodiments of my invention relate to additional details regarding the preferred catalytic ingredients, the concentration of components within the catalytic composite, the method of catalyst preparation, preferred processing techniques, process and reaction zone conditions and similar particulars which are hereinafter set forth.

Catalytic composites, tailored for the conversion of hydrocarbonaceous material and particularly those intended for utilization in an aromatic conversion process, have traditionally consisted of metallic elements chosen from Group VIII of the Periodic Table; however, metallic components from Group VIB are quite often incorporated therein.

I have found that a particularly effective zeolite-nickel-molybdenum-platinum catalyst can be prepared when the platinum content of the finished catalyst is maintained within the critical range of from about 0.2 to about 0.5 weight percent. Thus, it is now possible to prepare a more active and stable aromatic conversion catalyst.

As is customary in the art of catalysis, when referring to the catalytically active metal, or metals, it is intended to encompass the existence of such metal in the elemental state or in some form such as an oxide, sulfide, halide, etc. Regardless of the state in which the metallic components actually exist, the concentrations are computed as if they existed in the elemental state.

The zeolite carrier material may be prepared and utilized as spheres, pills, pellets, extrudates, granules, etc. The carrier material may be prepared in any suitable manner and may be activated prior to use by one or more treatments including drying, calcination, steaming, etc. Although generally existing in some combined form, the concentration of the catalytically active metallic components is calculated on the basis of the elemental metals. Suitable aromatic conversion catalysts will contain from about 0.01% to about 30% by weight of one or more metals, or compounds thereof. Another constituent of an aromatic conversion catalyst may include a halogen component. While the precise form of association of the halogen component of the carrier material is not accurately known, it is customary in the art to refer to the halogen component as being combined with the carrier or with the other ingredients of the catalyst therein. Combined halogen may be either fluorine, chlorine, iodine, bromine or mixtures thereof; of these, fluorine and chlorine are particularly preferred. The halogen will be composited with the carrier material in such a manner as results in a final catalytic composite containing from about 0.1% to about 2% by weight of a halogen component, calculated as the element.

The metallic components may be incorporated within the catalytic composite in any suitable manner including ion-exchange or impregnation of the carrier, and either after or before calcination. The preferred method for the incorporation of the metallic components is to impregnate the carrier material with an aqueous solution of nickel and molybdenum salts and then after drying and calcining, the platinum component is added with a separate impregnation with an aqueous solution of a chloroplatinic acid. Although the metallic components may be incorporated in any manner, it is believed that the two-step impregnation method hereinabove described yields a superior aromatic conversion catalyst. Even though the reasons for such a superior catalyst are uncertain, it is believed that the incorporation of the platinum metal component subsequent to the incorporation of the molybdenum component results in the construction of the most favorable metallic clusters utilized in aromatic conversion reactions.

Following the incorporation of the metallic components, the carrier material is dried and subjected to a high temperature calcination or oxidation technique at a temperature of about 750° F. to about 1000° F. One particularly preferred catalyst preparation technique involves the water-free reduction of the calcined composite. This particular step is designed to insure a more uniform and finely divided dispersion of the metallic components throughout the carrier material. Substantially pure and dry hydrogen, containing less than 30 volume ppm. of water is utilized as the reducing agent. The reduced catalytic composite may then subjected to a presulfiding technique to incorporate from about 0.05% to about 3.0% by weight of sulfur, on an elemental basis, within the final catalytic composite.

The ratios of reactants and other reaction conditions which occur when alkylating benzene with propylene are basically those well known in the art. Pressures may range from 1 to 100 atmospheres, or even higher. It is desirable to maintain pressure high enough to have a liquid phase in the reaction zone. Although it is possible to operate at very high pressure, little advantage is gained thereby, in fact, an increase in pressure seems to have a harmful effect. High pressure does not seem to effect the selectivity of the reaction to produce cumene, but rather seems to encourage the formation of non-aromatic compounds, possibly propylene trimers. Thus, operation at pressure above around 500 atm leads to the production of trace amounts of non-aromatic compounds, as determined by gas chromatography. Operation at pressures lower than 50 atm eliminated these. Preferred pressure seems to be around 20 to 60 atm, with an optimum pressure of about 35 atm.

Temperature effects both the conversion and selectivity of the reaction. Temperature may range between ambient and 250° C. At very low temperatures, the catalyst is not sufficiently active to permit the desired reaction to proceed at a satisfactory rate. At very high temperatures, it is believed that the catalyst may be damaged by formation of carbonaceous materials on the catalyst.

If the reaction is kinetically controlled, an increase in temperature should increase the rate of reaction. As a general statement, this is true, but the temperature dependence is not as large as expected, so the reaction may be limited by mass transport of reactants and products to and from the catalyst surface. Preferred operating temperatures seem to be about 100° to 200° C. It was difficult to pick an optimum temperature, but this may be because conversion of olefins was so high. Further studies, with less conversion, may indicate an optimum temperature for this reaction.

The catalyst may be disposed in a reactor vessel as a fixed, fluidized or moving bed of catalyst. The reactants may contact the catalyst in upflow, downflow or crossflow fashion, though upflow of reactants over a fixed bed of catalyst is preferred.

The liquid hourly space velocity in the reactor may range from 0.1 to 20. However, higher LHSV is possible depending on the desired conversion level of propylene. Because catalyst of the present invention is very active for the alkylation reaction, significantly higher space velocities are possible then when using some prior art catalysts, e.g., SPA. To some extent, the liquid hourly space velocity is related to temperature in the reaction zone, in general, a higher LHSV will require higher temperature operation.

As used herein, conversion refers to the disappearance of reactants. Thus, conversion refers to percent disappearance of propylene feed. Selectively means the amount of cumene produced per mole of propylene that was consumed, expressed as percent. Thus 90% conversion means that for every 100 moles of propylene entering the reactor, 90 moles were converted to something else. A selectivity of 80% would mean that 72 moles of cumene were formed, e.g., that 80% of the 90 moles of propylene consumed were converted to cumene.

Although the method of preparing the catalyst, and careful selection of operating conditions within the ranges hereinbefore set forth, extend the effective life of the catalyst composite, regeneration thereof may eventually become desired due to the natural deterioration of the catalytically active metallic components. The catalytic composite is readily regenerated by treating the same in an oxidizing atmosphere, at a temperature of from about 750° F. to about 850° F., and burning coke and other heavy hydrocarbonaceous material therefrom. The catalyst composite may then be subjected to the reducing in hydrogen, in situ, at a temperature up to about 1000° F. If desirable, the catalyst may then be sulfided in the same manner as fresh catalyst as hereinbefore described.

The drawing included in the instant application is for the purpose of visually demonstrating the improvements and advantages afforded by the manufacture of zeolite-nickel-molybdenum-platinum catalyst according to the present invention.

The following examples are presented in illustration of the catalyst of this invention and is not intended as an undue limitation on the generally broad scope of the invention as set out in the appended claims.

EXAMPLE I

This example describes the preparation and testing of four zeolite-nickel-molybdenum-platinum catalysts each of which has an extruded carrier material containing 25% alumina and 75% faujasite, 5% nickel, 2% molybdenum and which contain 0.2, 0.3, 0.4 and 0.5 weight percent platinum, respectively. The extruded alumina-faujasite carrier material was initially impregnated with an aqueous solution containing soluble nickel and molybdenum salts in sufficient concentration to yield a finished catalyst with the desired nickel and molybdenum concentrations. The freshly impregnated support was then dried at about 100° C. and calcined at about 500° C. The resulting dried and calcined carrier material containing 5% nickel and 2% molybdenum was divided into five batches and four batches were impregnated with an aqueous chloroplatinic acid solution with a concentration sufficient to yield a finished catalyst with 0.2, 0.3, 0.4 and 0.5 weight percent platinum, respectively. The platinum impregnated catalyst were then dried and calcined at 100° C. and 500° C., respectively. The fifth batch was not impregnated with platinum and served as a reference catalyst for comparison purposes.

A portion of each of the five hereinabove described batches of catalyst was then used in the hydrocracking of a vacuum gas oil whose properties are summarized in Table I.

TABLE I

| PROPERTIES OF VACUUM GAS OIL | |
|---|---|
| API° Gravity at 60° F. | 33.5 |
| Distillation, °F. | |
| IBP | 290 |
| 10 | 455 |
| 30 | 596 |
| 50 | 697 |
| 70 | 762 |
| 90 | 830 |
| 95 | 870 |
| E.P. | 930 |
| % Over | 99 |
| Total Sulfur, wt. % | 0.22 |
| Total Nitrogen, ppm. | 3 |

In each case, the vacuum gas oil was processed with a reactor pressure of 1500 psig., a liquid hourly space velocity of 2.0, a hydrogen circulation rate of 10,000 scf./bbl. and at a peak catalyst bed temperature of 315° C.

The hydrocracking ability of the non-platinum containing reference catalyst was arbitrarily assigned a Relative Hydrocracking Activity of 100. Platinum containing catalysts comprising 0.2, 0.3, 0.4 and 0.5 weight percent platinum and hereinafter referred to as Catalysts 1, 2, 3, and 4, respectively, were utilized to hydrocrack the hereinbefore described vacuum gas oil and these four catalysts exhibited a Relative Hydrocracking Activity of 133, 152, 165, and 129, respectively. These data are presented in tabular form in Table II and in graphical form in the accompanying drawing.

TABLE II

EVALUATION FOR HYDROCRACKING ACTIVITY

| Catalyst Identity | 1 | 2 | 3 | 4 |
|---|---|---|---|---|
| Platinum Concentration, wt. % | 0.2 | 0.3 | 0.4 | 0.5 |
| Relative Hydrocracking Activity | 133 | 152 | 165 | 129 |

From the data presented in foregoing Table II and with reference to the accompanying drawing, it will be seen that the four catalysts' increasing concentrations of platinum, the latter ranging from 0.2% to 0.5% by weight, did not demonstrate linearly increasing Relative Hydrocracking Activity. This is clearly brought out upon comparing the results obtained through the use of Catalysts 1, 2, 3 and 4 which indicated a Relative Hydrocracking Activity of 133, 152, 165 and 129 respectively, for the conversion of vacuum gas oil to lower boiling hydrocarbons. Datum points 1, 2, 3 and 4 in the drawing are representative of the results obtained with Catalysts 1, 2, 3 and 4, respectively. These data were employed in preparing curve 5 of the drawing, which curve clearly illustrates the criticality attached to the platinum concentration within the range of about 0.2% to about 0.5% by weight, in order to produce a hydrocracking catalyst with superior performance characteristics. The additional economic advantages afforded through this particular result will be readily recognized by those possessing skill within the art of petroleum refining processes.

EXAMPLE II

This example describes the preparation and testing of three zeolite-nickel-molybdenum-platinum catalysts each of which has an extruded carrier material containing 25% alumina and 75% faujasite, 5% nickel, 2% molybdenum and which contain 0.2 wt. % platinum, 0.5 wt. % platinum and 0.4 wt. % palladium, respectively. The extruded alumina-faujasite carrier material was prepared in exactly the same manner as hereinabove described in Example I. The 5% nickel and 2% molybdenum was incorporated with said carrier material, also, as hereinabove described in Example I. Two portions of the resulting dried and calcined carrier material containing 5% nickel and 2% molybdenum were impregnated with an aqueous chloroplatinic acid solution with a concentration sufficient to yield a finished catalyst with 0.2 and 0.5 wt. % platinum, respectively. A third portion of the dried and calcined carrier material containing 5% nickel and 2% molybdenum was impregnated with an aqueous solution containing palladium chloride with a concentration sufficient to yield a finished catalyst with 0.4 wt. % palladium. Each of the three portions of the impregnated catalysts were then dried and calcined at 100° C. and 500° C., respectively.

The three portions of catalyst prepared as hereinabove described were then used in the hydrocracking of a vacuum gas oil whose properties are summarized in Table I. In each case, the gas oil was processed with a reactor pressure of 1500 psig., a liquid hourly space velocity of 2.0, a hydrogen circulation rate of 10,000 scf./bbl. and at a peak catalyst bed temperature of 325° C. It will be noted that catalyst bed temperature of Example I was 315° C.

The hydrocracking ability of the non-platinum and non-palladium reference catalyst of Example I was arbitrarily assigned a Relative Hydrocracking Activity of 100. Platinum containing catalysts comprising 0.2 and 0.5 wt. % platinum and palladium containing catalyst comprising 0.4 wt. % palladium hereinafter referred to as Catalysts 5, 6 and 7, respectively, were utilized to hydrocrack the hereinbefore described vacuum gas oil and these three catalysts exhibited a Relative Hydrocracking Activity of 141, 163 and 105, respectively. These data are presented in tabular form in Table III.

TABLE III

| Evaluation for Hydrocracking Activity | | | |
|---|---|---|---|
| Catalyst Identity | 5 | 6 | 7 |
| Platinum Concentration, wt. % | 0.2 | 0.5 | — |
| Palladium Concentration, wt. % | — | — | 0.4 |
| Relative Hydrocracking Activity | 141 | 163 | 105 |

The data presented in foregoing Table III illustrate that a platinum containing catalyst in the claimed critical range, viz., about 0.2 to about 0.5 wt. %, exhibits unexpected and greatly superior catalytic activity when compared with a catalyst containing palladium within the same range. When a Relative Activity comparison of 163 versus 105 can be demonstrated in the realm of catalysis, those skilled in the art will readily recognize the economic advantages afforded through the catalyst of the present invention and the fact that a randomly selected component from a Group VIII or any other group will not necessarily exhibit the desired catalytic characteristics.

Example III

A portion of catalyst prepared in Example I and designated Catalyst No. 3 is selected to alkylate benzene and propylene. This catalyst is maintained as a fixed catalyst bed having a volume of 50 cc. The reactants, i.e., benzene and propylene are passed upflow over the catalyst bed. The benzene is dried by circulating it over high surface area sodium. Pure propylene is dried by passing it over type 4-A molecular sieves. The benzene and propylene are mixed in a 8:1 ratio, respectively, and the resulting mixture is charged to the reactor. The reaction zone is maintained at conditions which include a temperature of 180° C., a pressure of 35 atmospheres and liquid hourly space velocity of 2. The reactor is started up full of liquid benzene and the mixture of propylene and benzene is added. It is believed that if during start-up propylene alone is charged, or even propylene and benzene is charged simultaneously, high molecular weight polymers may form. The reaction zone effluent is recovered and an analysis of the effluent indicates the presence of cumene.

The foregoing specification and examples clearly illustrate the improvements encompassed by the present invention and the benefits to be afforded a process for the conversion of aromatics.

I claim as my invention:

1. A process for the catalytic conversion of an aromatic hydrocarbon comprising contacting the aromatic hydrocarbon with a reactant in the presence of a catalytic composite comprising a combination of a nickel component, a molybdenum component and a platinum component with a zeolitic carrier material wherein said platinum component is present in an amount sufficient to result in the composite containing, on an elemental basis, about 0.2 to about 0.5 percent by weight platinum, and recovering a converted aromatic hydrocarbon as a product of the process.

2. The process of claim 1 wherein the aromatic hydrocarbon is selected from the group consisting of benzene, toluene, ethylbenzene, xylene and cumene isomers.

3. The process of claim 1 wherein the reactant is selected from the group consisting of an olefin, an alkylhalide, and aromatic hydrocarbons.

4. The process of claim 1 wherein the conversion reaction which occurs in alkylation of an aromatic compound with an alkylating agent.

5. The process of claim 4 wherein benzene is alkylated with an olefin selected from the group of ethylene and propylene.

6. The process of claim 4 wherein benzene is alkylated with an olefin selected from the group of $C_8$ to $C_{18}$ olefins.

7. The process of claim 1 wherein the conversion reaction which occurs in transalkylation of alkylaromatic compounds.

8. The process of claim 7 wherein toluene is transalkylated to benzene and xylene.

9. The process of claim 1 wherein said zeolitic carrier material comprises faujasite and alumina.